United States Patent
Kozin

(10) Patent No.: US 10,010,637 B2
(45) Date of Patent: Jul. 3, 2018

(54) THERMALLY SHRINKABLE WRAPPER, IN PARTICULAR FOR USE IN STERILIZATION PROCESS

(71) Applicant: Peter Kozin, Ljubljana (SI)

(72) Inventor: Peter Kozin, Ljubljana (SI)

( * ) Notice: Subject to any disclaimer, the term of this patent is extended or adjusted under 35 U.S.C. 154(b) by 125 days.

(21) Appl. No.: 15/034,591

(22) PCT Filed: Nov. 3, 2014

(86) PCT No.: PCT/SI2014/000063
§ 371 (c)(1),
(2) Date: May 5, 2016

(87) PCT Pub. No.: WO2015/069196
PCT Pub. Date: May 14, 2015

(65) Prior Publication Data
US 2016/0271283 A1 Sep. 22, 2016

(30) Foreign Application Priority Data

Nov. 5, 2013 (SI) .................................... 201300365
Oct. 27, 2014 (SI) .................................... 201400396

(51) Int. Cl.
*A61L 2/26* (2006.01)
*B32B 27/36* (2006.01)
(Continued)

(52) U.S. Cl.
CPC ................... *A61L 2/26* (2013.01); *A61L 2/06* (2013.01); *B32B 5/022* (2013.01); *B32B 27/36* (2013.01);
(Continued)

(58) Field of Classification Search
CPC ..... A61L 2/26; A61L 2202/181; B32B 27/36; B32B 5/022
See application file for complete search history.

(56) References Cited

U.S. PATENT DOCUMENTS 3,073,507 A 1/1963 Trewella et al.
5,922,162 A 7/1999 Brugger et al.
(Continued)

FOREIGN PATENT DOCUMENTS

FR 2543110 A1 9/1984

OTHER PUBLICATIONS

International Search Report and Written Report issued in PCT/SI2014/000063 dated May 11, 2015 (11 pages).

*Primary Examiner* — Kevin Joyner
(74) *Attorney, Agent, or Firm* — Haynes and Boone, LLP; William B. Nash; Joseph R. Mencher

(57) ABSTRACT

A thermally shrinkable wrapper, in particular for use in sterilization processes, includes a first layer of a thermally shrinkable film in the form of a continuous band having a pre-determined width and at least approximately parallel longitudinal edges that define a longitudinal direction of the wrapper. A second layer of a thermally shrinkable film in the form of a continuous band having a pre-determined width and at least approximately parallel longitudinal edges, is placed over said first layer so that the longitudinal edges of the first and said second layer are at least approximately aligned with respect to each other. A pair of bearing bands provided by a thermally non-shrinkable material are embedded and welded between the first layer and the second layer in the area of their aligned longitudinal edges.

20 Claims, 1 Drawing Sheet

(51) Int. Cl.
  *B32B 5/02* (2006.01)
  *A61L 2/06* (2006.01)
  *A61B 50/30* (2016.01)
(52) U.S. Cl.
  CPC ... *A61B 2050/314* (2016.02); *A61L 2202/181* (2013.01); *A61L 2202/24* (2013.01); *B32B 2307/736* (2013.01); *B32B 2535/00* (2013.01)

(56) References Cited

U.S. PATENT DOCUMENTS 6,251,489 B1 * 6/2001 Weiss ................. A61L 2/07
 206/438
2013/0272630 A1 10/2013 Thomas

* cited by examiner

THERMALLY SHRINKABLE WRAPPER, IN PARTICULAR FOR USE IN STERILIZATION PROCESS

CROSS-REFERENCE TO RELATED APPLICATION

This application is a United States national phase application of co-pending international patent application number PCT/SI2014/000063, filed Nov. 3, 2014, which claims the benefit of Slovenia Application No. P-201300365 filed Nov. 5, 2013, and Slovenia Application No. P-201400396 filed Oct. 27, 2014, of which are hereby incorporated by reference in its entirety.

BACKGROUND

Pursuant to IPC, the invention refers to processing of plastics, namely to formation or interconnecting and subsequent treatment of formed products, and quite exactly to connecting each product by means of a thermally shrinkable film. Moreover, the invention may also refer to multi-layered packaging containing artificial resins, in particular polyester.

The purpose of the invention is to create a thermally shrinkable wrapper, which should be suitable for use in sterilization process and will at least in transversal direction be sufficiently strong for the purpose of binding of object wrapped therewith, and which should be also easily removable after the shrinking thereof.

The invention refers to a packaging in the form of a sleeve, which is made of a thermally shrinkable material, which is shrank by means of thermal energy during a process of sterilization, so that the sterilization package is firmly bound, although the sterilization media is still allowed to penetrate towards the interior of said package.

In the process of sterilization of heavier units of surgical instruments, which are usually named sets or nets, a double-layered wrapping into sheets of sterilization paper or any other suitable sterilization material is used. Special adhesive bands, which are suitable for use in conditions during said process of sterilization, are used in order to prevent unwinding of such bundles.

Classical wrapping as commonly used packing into said flexible sterilization packaging excels essential benefits when compared with other methods of sterilization packing due to relatively large dimensions, which by unwinding enable covering of working surfaces and herewith also protection of a sterile working area. The main deficiency of such classical wrapping results in a relatively complicated process of manual wrapping, which essentially depends in a human factor. Another deficiency of such classical wrapping furthermore results from the use of adhesive bands, which sometimes stick out due to conditions in the sterilization process, so that the sterilization bundles become unwound, and are moreover also difficulty removed in situ, which may jeopardize aseptic conditions. Parameters of packing each sterile items, which are prescribed by IS0-11607 standard, however cannot be assured by using such classic wrapping.

The proposed wrapper is produced in the form of a sleeve with appropriate dimensions, which is then cut by user to each desired length, which is adjusted to each sterilization packaging, and by which a classically wrapped packaging is dressed prior to inserting it into each sterilization appliance for the purpose of sterilization. During sterilization at increased temperature, the wrapper is shrank, by which the packaging is compressed, by which then the windings of said classic sterilization wrapper are fixed. Thanks to sealing and shrinking, the human factor is eliminated, and moreover, there is no need to use said risky adhesive bands, by which the requirements as prescribed in said IS0-11607 can easily be fulfilled.

The wrapper consists of a material, which is resistant during all stages of each process of sterilization. Penetration of each sterilization media is achieved by means of perforations available on said thermally shrinkable material. During the process of sterilization, the material is initially shrank, by which said perforations open and enable penetration of said sterilization media during the process of sterilization.

Aseptic presentation in situ is easily achieved by means of one or more longitudinal bands, which are easily removable by simply tearing-off, upon which a sterile packaging is released and is suitable for further unwinding and presentation.

A wrapper in accordance with a further aspect of the invention can be manufactured in combination with a barrier layer, wherein such barrier material is intended to prevent from intrusion of microorganisms. A thermally shrinkable material then establishes a mechanical protection of said barrier layer, wherein said thermally shrinkable material serves as a stand-alone system of sterilization packing. Such combination is achieved either by laminating, welding or any other combining of materials in such manner, that a perfect barrier against intrusion of microorganisms is achieved. An important innovation in manufacturing of such packaging relates to longitudinal ultrasonic welding of two thermally shrinkable layers with an intermediate band, which consists of a thermally stable material and is inserted there-between in order to reinforce the weld, which is however easily removable by simply tearing-off: by which the packaging is then open. The lateral weld is actually a weld, by which three layers are interconnected, namely a top thermally shrinkable layer, a thermally stable intermediate layer, as well as a bottom thermally shrinkable layer. Each weld in such combination is extremely strong in the transversal direction and enables each desired compression and fixation of the package, but is also pretty weak in view of cutting effect in the longitudinal direction, which is used for opening the package, since by simply tensioning one terminal portion of the band the longitudinal weld is tear-on which enables perfectly aseptic opening of the package.

The invention provides a sterilization wrapper, which consists of a thermally shrinkable material and is characterized by shrinking by means of thermal energy during the process of sterilization for the purposes of fixation of a primary sterilization wrapper.

The invention further provides a packaging in accordance with previously mentioned features, which is manufactured in combination with a barrier material in such manner that said barrier materials prevents from intrusion of microorganisms towards the interior of each sterile package, for the purpose that such packaging represents a stand-alone system of packing in each process of sterilization.

The invention further provides ultrasonic welding by using an intermediate band consisting of a thermally stable material and being inseiled between two layers of a thermally shrinkable material, which enables realization of welds, which are sufficiently strong in the transversal direction, and on the other hand easily opening of each package by means of tearing-off and disruption of the welds in the longitudinal direction thereof. Provided is also opening of a thermally shrinkable package by means of tearing-off the weld, which is reinforced by a thermally stable material extending in the longitudinal direction of the weld, by means of cutting effect.

A thermally shrinkable wrapper is disclosed in WO 2005/011978 A1, JP 11227805 and U.S. Pat. No. 3,429,433.

In accordance with the invention, the previously mentioned problem is solved by means of a thermally shrinkable wrapper, which is in particular suitable for use in sterilization process and which comprises:

a first layer consisting of thermally shrinkable film in the form of endless band of pre-determined width and with at least approximately linear longitudinal edges defining a longitudinal direction of the wrapper a second layer consisting of thermally shrinkable film in the form of endless band of pre-determined width and with two at least approximately linear longitudinal edges, which is placed over said first layer, so that both pairs of longitudinal edges are at least approximately aligned with each other;

a pair of bearing bands consisting of thermally non-shrinkable material, wherein each of them is integrated and welded between said first layer and said second layer in the area of their aligned longitudinal edges, wherein each of said thermally shrinkable layers is furnished with a plurality of perforations, which are arranged in the form of an uniform raster along the lines, which extend equidistantly with respect to each other in the transversal direction of the wrapper and are also equidistantly arranged in the longitudinal direction of the wrapper, and wherein each connecting area between each bearing band and said first and second layer is formed of groups of welds, which are equidistantly spaced apart from each other in the longitudinal direction of the wrapper and are present on both bearing bands as well as on both layers adjacent to said longitudinal edges thereof, so that each group of welds comprises at least two welds, which each per se extend in the longitudinal direction of the wrapper and are spaced apart from each other in the transversal direction of said wrapper.

In a preferred embodiment of the invention, each of said perforations is conceived in the form of letter S and comprises a linear central section, which extend in the transversal direction of the wrapper, and substantially semi-circular terminal sections, which are in the longitudinal direction of the wrapper arranged on different sides of said central section, wherein the orientation of said terminal regions remains equal in all perforations, which are repeated both in longitudinal direction and transversal direction of the wrapper.

It is in particular preferred, when each group of welds comprises at least three linear welds, which are aligned and equidistantly spaced apart from each other in the transversal direction and Each weld is selected from the group, which includes laser welds and ultrasonic welds.

Each of said thermally shrinkable layers consists of material, which is independently selected from the group, which includes polyethylene (PE), high-density polyethylene (HDPE), low-density polyethylene (LDPE), polypropylene (PP) and polyolefin. When the wrapper is used in process of sterilization, the invention is further characterized in that each of said thermally shrinkable layers consists of material, which is shrinkable at temperature below the temperature, which is required for sterilization of each substance or each object wrapped with said wrapper.

Each of said bearing bands consists of a thermally non-shrinkable non-woven material, in which polyester is dominant.

The invention further provides use of the wrapper according to previously stated features a process of sterilization of surgical instruments.

The use of such wrapper is moreover foreseen in a process of sterilization of surgical instruments, which are placed on a plate and wrapped with a woven or non-woven flexible material, which is suitable for application in the process of sterilization of surgical instruments.

BRIEF DESCRIPTION OF DRAWINGS

The invention will be described on the basis of an embodiment, which is presented in the enclosed drawings, where.

DETAILED DESCRIPTION

Figure 1:
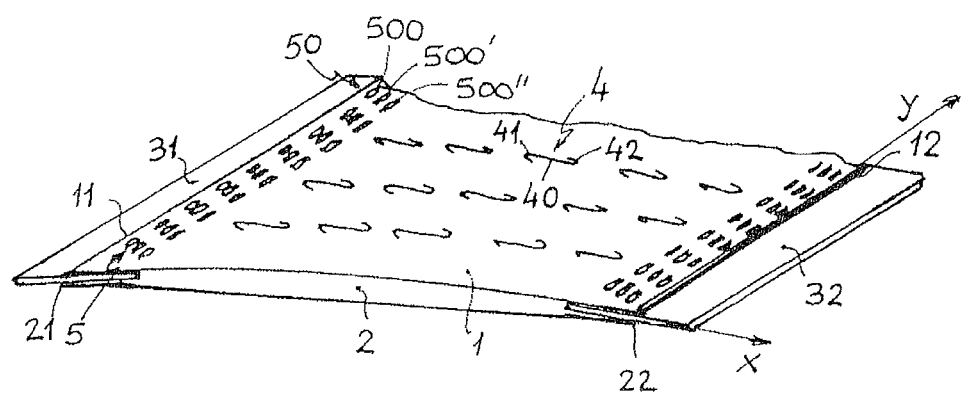
FIG. 1 is an isometric top view of a thermally shrinkable wrapper.

A thermally shrinkable wrapper, in particular for use in sterilization process, in accordance with the proposed invention consists of a first layer 1 of a thermally shrinkable film in the form of endless band having a pre-determined width B and at least approximately linear longitudinal edges 11, 12, which define the longitudinal direction Y of the wrapper, as well as of a second layer 2 of said thermally shrinkable film in the form of endless band having a pre-determined width B and at least approximately linear longitudinal edges 21, 22, which is placed above said first layer 1, so that the longitudinal edges 11, 12; 21, 22 of said first layer and said second layer 2 are at least approximately aligned, and moreover also of a pair of bearing bands 31, 32, which consist of a thermally non-shrinkable material and are each per se inserted and welded between said first layer 1 and said second layer 2 in the area of said longitudinal edges 11, 12; 21, 22 thereof.

Each of said thermally shrinkable layers 1, 2 is furnished with a plurality of perforations 4, which are arranged in the form of an uniform raster along the lines, which extend at equal distances apart from each other in the transversal direction X of the wrapper and at equal distances also in the longitudinal direction Y of the wrapper, wherein each connecting area 5 between each bearing band 31, 32 and the first and second layer 1, 2 is realized by means of groups 50 of welds 500, which are arranged on both layers 1, 2 adjacent to said longitudinal edges 11, 12; 21, 22 thereof and simultaneously on each belonging bearing band 31, 32, so that each group 50 of welds 500 comprises at least two linear welds 500, 500', 500", which extend in the longitudinal direction Y of the wrapper and are spaced apart from each other in the transversal direction X of said wrapper.

In a preferred embodiment of the invention (FIGS. 1 and 2), each of said perforations 4 in the form of letter S consists of a linear central section 40, which extends in the transversal direction X of the wrapper, as well as two essentially semi-circular terminal sections 41, 42, which are in the longitudinal direction Y arranged on different sides of said central section 40, and wherein the orientation of said terminal sections 41, 42 is the same by all perforations 4, which are periodically repeated in the transversal direction X and the longitudinal direction Y of the wrapper.

Figure 2:
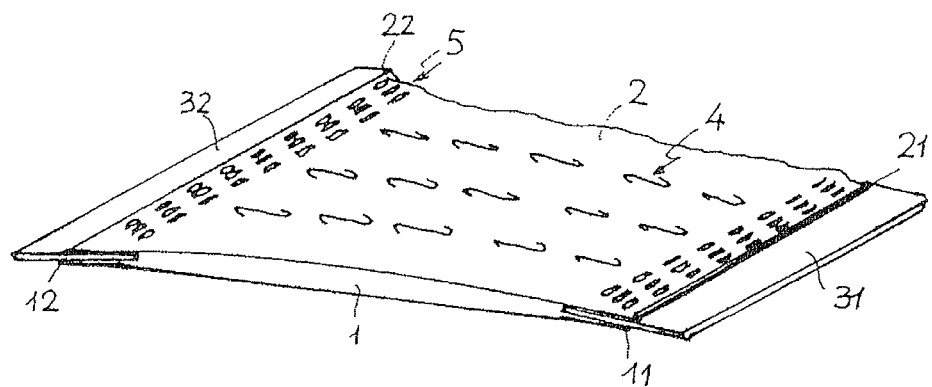
FIG. 2 is an isometric bottom view of said wrapper.

Each group 50 of welds 500, 500', 500" preferably comprises at least three aligned linear welds 500, 500', 500", which each per se extend in the longitudinal direction Y of the wrapper and which are equally spaced apart from each other in the transversal direction X of the wrapper. The embodiment according to FIGS. 1 and 2 provides that each group 50 comprises three welds 500, 500', 500". In this, each weld 500, 500', 500" is either an ultrasonic weld or a laser weld.

Each of said thermally shrinkable layers 1, 2 consists of a material, which is independently selected from the group which includes polyethylene (PE), high-density polyethylene (HDPE), low-density polyethylene (LDPE), polypropylene (PP) and polyolefin, while on the other hand each bearing band 31, 32 consists of a thermally non-shrinkable non-woven material, in which polyester is dominant.

Whenever said wrapper is used in sterilization process, each of said thermally shrinkable layers should preferably consist of material, which is shrinkable at the temperature below the temperature, which is required in each process of sterilization of certain substance or certain object, which is wrapped by means of such wrapper.

The invention also provides the use of such wrapper in a process of sterilization of surgical instruments, wherein said instruments are initially placed onto a plate and then wrapped with a primary wrapper consisting of woven or non-woven material, which is suitable for use in sterilization of surgical instruments, and upon that such package is wrapped with the thermally shrinkable wrapper in accordance with the invention.

As soon as the wrapper together with each content is placed into an area with appropriately increased temperature, in particular into a sterilization chamber, said thermally shrinkable layers 1, 2 each per se starts shrinking, wherein the wrapper excels a required strength at least in the transversal direction. Due to the presence of said bearing bands 31, 32, said perforations 4 become open, by which the sterilization media is enabled to pass there-through. As soon as the layers 1, 2 are shrank, the wrapper can be easily removed by means of tearing-off the bearing bands 31, 32, which is due to the previously described configuration of welds 500, 500', 500" feasible in a really simple manner, namely by pulling each band 31, 32 in the transversal direction X of the wrapper.

The invention claimed is:

1. A thermally shrinkable wrapper system, comprising:
a first layer that is provided by a thermally shrinkable film, that includes a pair of first layer edges that are located on opposite sides of the first layer, and that defines a plurality of spaced-apart first layer perforations that are located between the pair of first layer edges;
a second layer that is provided by a thermally shrinkable film, that includes a pair of second layer edges that are located on opposite sides of the second layer, and that defines a plurality of spaced-apart second layer perforations that are located between the pair of second layer edges, wherein the first layer is positioned adjacent the second layer such that each of the pair of first layer edges are aligned with respective edges in the pair of second layer edges to provide a first edge pair and a second edge pair;
a first band that is provided by a thermally non-shrinkable material and that is coupled between the first edge pair by a plurality of spaced-apart first band welds that are provided adjacent the first edge pair and between the first band and each of the first layer and the second layer; and
a second band that is provided by a thermally non-shinkable material and that is coupled between the second edge pair by a plurality of spaced-apart second band welds that are provided adjacent the second edge pair and between the second band and each of the first layer and the second layer.

2. The system of claim 1, wherein each of the plurality of perforations includes a linear central section and substantially semi-circular terminal sections on each end of the linear central section.

3. The system of claim 1, wherein the plurality of first band welds include at least two linear first band weld groups that are substantially perpendicular to each other, and wherein the plurality of second band welds include at least two linear second band weld groups that are substantially perpendicular to each other.

4. The system of claim 1, wherein each of the plurality of first band welds and each of the plurality of second band welds is one of a laser weld and an ultrasonic weld.

5. The system of claim 1, wherein the thermally shrinkable film that provides the first layer and the second layer includes a material that is selected from the group that includes polyethylene (PE), high-density polyethylene (HDPE), low-density polyethylene (LDPE), polypropylene (PP) and polyolefin.

6. The system of claim 1, wherein the thermally shrinkable film that provides the first layer and the second layer includes a material that is configured to shrink at a first temperature that is less than a second temperature that is required for sterilization of an object that is to be wrapped using the first layer and the second layer.

7. The system of claim 1, wherein the first band and the second band include the thermally non-shrinkable material that includes a non-woven polyester.

8. A sterilization method, comprising:
positioning an object in a wrapper system that includes:
a first layer and a second layer that are each provided by a thermally shrinkable film, that are aligned along respective edges to provide a first edge pair and a second edge pair, and that each define a plurality of spaced-apart perforations;
a first band that is provided by a thermally non-shrinkable material and that is coupled between the first edge pair by a plurality of spaced-apart first band welds; and
a second band that is provided by a thermally non-shrinkable material and that is coupled between the second edge pair by a plurality of spaced-apart second band welds;
increasing a temperature of the wrapper system to cause the first layer and the second layer to shrink such that at least some of the plurality of spaced-apart perforations to open to provide a plurality of perforation openings and the object extends through the perforation openings;
disconnecting at least one of 1) the first band from the wrapper system along the plurality of first band welds, and 2) the second band from the wrapper system along the plurality of second band welds; and
removing the object from the wrapper system.

9. The method of claim 8, wherein each of the plurality of perforations includes a linear central section and substantially semi-circular terminal sections on each end of the linear central section.

10. The method of claim 8, wherein the plurality of first band welds include at least two linear first band weld groups that are substantially perpendicular to each other, and wherein the plurality of second band welds include at least two linear second band weld groups that are substantially perpendicular to each other.

11. The method of claim 8, wherein each of the plurality of first band welds and each of the plurality of second band welds is one of a laser weld and an ultrasonic weld.

12. The method of claim 8, wherein the thermally shrinkable film that provides the first layer and the second layer includes a material that is selected from the group that includes polyethylene (PE), high-density polyethylene (HDPE), low-density polyethylene (LDPE), polypropylene (PP) and polyolefin.

13. The method of claim 8, wherein the thermally shrinkable film that provides the first layer and the second layer includes a material that is configured to shrink at a first temperature that is less than a second temperature that is required for sterilization of the object.

14. The method of claim 8, wherein the first band and the second band include the thermally non-shrinkable material that includes a non-woven polyester.

15. A surgical instrument sterilization method, comprising:
    wrapping a surgical instrument in a primary sterilization wrapper to provide a wrapped surgical instrument;
    positioning the wrapped surgical instrument in a secondary thermally shrinkable wrapper system that includes:
        a first layer and a second layer that are each provided by a thermally shrinkable film, that are aligned along an edge to provide an edge pair, and that each define a plurality of spaced-apart perforations; and
        a band that is provided by a thermally non-shrinkable material and that is coupled between the edge pair by a plurality of spaced-apart band welds;
    positioning the wrapped surgical instrument in the secondary thermally shrinkable wrapper system in an oven;
    increasing a temperature of the oven such that the first layer and the second layer shrink and cause the wrapped surgical instrument to extend through at least some of the plurality of spaced-apart perforations, wherein the increase in temperature causes a sterilization of the surgical instrument;
    disconnecting the band from the secondary thermally shrinkable wrapper system along the plurality of band welds; and
    removing the surgical instrument from the wrapper system.

16. The method of claim 15, wherein each of the plurality of perforations includes a linear central section and substantially semi-circular terminal sections on each end of the linear central section.

17. The method of claim 15, wherein the plurality of band welds include at least two linear band weld groups that are substantially perpendicular to each other.

18. The method of claim 15, wherein each of the plurality of band welds is one of a laser weld and an ultrasonic weld.

19. The method of claim 15, wherein the thermally shrinkable film that provides the first layer and the second layer includes a material that is selected from the group that includes polyethylene (PE), high-density polyethylene (HDPE), low-density polyethylene (LDPE), polypropylene (PP) and polyolefin.

20. The method of claim 15, wherein the band includes the thermally non-shrinkable material that includes a non-woven polyester.

* * * * *

UNITED STATES PATENT AND TRADEMARK OFFICE
CERTIFICATE OF CORRECTION

PATENT NO. : 10,010,637 B2
APPLICATION NO. : 15/034591
DATED : July 3, 2018
INVENTOR(S) : Peter Kozin Page 1 of 1

It is certified that error appears in the above-identified patent and that said Letters Patent is hereby corrected as shown below:

In the Specification

In Column 2, Line 61: "inselied" should be --inserted--;

In Column 5, Line 66: "non-shinkable" should be --non-shrinkable--.

Signed and Sealed this
Twenty-eighth Day of August, 2018

Andrei Iancu
*Director of the United States Patent and Trademark Office*